(12) United States Patent
Ehring et al.

(10) Patent No.: US 9,322,772 B2
(45) Date of Patent: Apr. 26, 2016

(54) METHODS AND APPARATUS FOR MEASURING THE LIGHT ABSORBANCE OF A SUBSTANCE IN A SOLUTION

(71) Applicant: GE HEALTHCARE BIO-SCIENCES AB, Uppsala (SE)

(72) Inventors: Hanno Ehring, Uppsala (SE); Fredrik Lars Jarhede, Uppsala (SE); Erik Ostlund, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 14/404,860

(22) PCT Filed: May 30, 2013

(86) PCT No.: PCT/EP2013/061212
§ 371 (c)(1),
(2) Date: Dec. 1, 2014

(87) PCT Pub. No.: WO2013/178770
PCT Pub. Date: Dec. 5, 2013

(65) Prior Publication Data
US 2015/0153272 A1    Jun. 4, 2015

(30) Foreign Application Priority Data

May 31, 2012 (GB) .................................. 1209738.2

(51) Int. Cl.
*G01J 1/42* (2006.01)
*G01N 21/33* (2006.01)
(Continued)

(52) U.S. Cl.
CPC ............ *G01N 21/33* (2013.01); *G01N 21/3151* (2013.01); *G01N 30/74* (2013.01); *G01N 2021/3181* (2013.01); *G01N 2030/8827* (2013.01); *G01N 2201/062* (2013.01)

(58) Field of Classification Search
CPC .......................... G01N 21/314; G01N 21/3151
See application file for complete search history.

(56) References Cited

U.S. PATENT DOCUMENTS 5,408,326 A  4/1995 Wang
5,959,738 A  9/1999 Hafeman et al.
(Continued)

FOREIGN PATENT DOCUMENTS

DE  202009006771  11/2009
DE  102011012674   4/2012
(Continued)

OTHER PUBLICATIONS

Nagali et al., "Design of a diode-laser sensor to monitor wave vapor in high-pressure combustion gases," 1997, Applied Optics, vol. 36, No. 36, pp. 9518-9527.*
(Continued)

*Primary Examiner* — Kiho Kim
(74) *Attorney, Agent, or Firm* — Parks Wood LLC (57) ABSTRACT

Disclosed is an apparatus for measuring the absorbance of a substance in a solution, comprising: i) a sample cell (30) of known path length (b) for containing said solution (S), said cell being transparent to light of a predefined wavelength spectrum; ii) plural LED's each being independently operable by means of a controller (25) each for emitting light, within said predefined wavelength spectrum, along a light path; iii) a band pass filter (22) in the light path; iv) a beam splitter (24) for dividing light from said source propagating along the path into a first portion and a second portion, said first portion being directable by the beam splitter toward a reference detector (42) and said second portion being directable into the cell (30); v) a reference detector (42) for detecting the intensity of said first portion of light directed by said beam splitter; and vi) a sample detector (40) for detecting the intensity of the second portion propagating from the cell; the apparatus allowing a sample in the cell to be inexpensively subjected to more than one wavelength of light for quicker or more accurate analysis.

15 Claims, 4 Drawing Sheets

(51) Int. Cl.
*G01N 30/74* (2006.01)
*G01N 21/31* (2006.01)
*G01N 30/88* (2006.01)

(56) References Cited

U.S. PATENT DOCUMENTS

| | | | |
|---|---|---|---|
| 6,741,875 B1 | 5/2004 | Pawluczyk et al. | |
| 7,122,799 B2 | 10/2006 | Hsieh et al. | |
| 7,840,360 B1* | 11/2010 | Micheels | G01J 3/42 250/223 B |
| 2002/0074513 A1* | 6/2002 | Abel et al. | 250/458.1 |
| 2005/0225745 A1* | 10/2005 | Nagai | G01N 15/147 356/73 |
| 2007/0229830 A1* | 10/2007 | Yamamoto | G01N 21/82 356/414 |
| 2008/0275659 A1* | 11/2008 | Miller | G01N 21/21 702/84 |
| 2008/0316486 A1* | 12/2008 | Nishiuma | G01N 21/21 356/364 |
| 2009/0068747 A1* | 3/2009 | Iten | 436/35 |
| 2009/0091718 A1* | 4/2009 | Obi | G03B 21/56 355/30 |
| 2013/0261413 A1* | 10/2013 | Kawahara | A61B 5/1455 600/316 |

FOREIGN PATENT DOCUMENTS

| | | | |
|---|---|---|---|
| DE | 102011008482 | 11/2012 | |
| EP | 1730495 | 11/2011 | |
| GB | 2462518 | 2/2010 | |
| JP | 2002005826 A * | 1/2002 | G01N 21/33 |
| JP | 2004147706 | 5/2004 | |
| WO | 2007062800 | 6/2007 | |

OTHER PUBLICATIONS

Dasgupta et al. "Light Emitting Diode BAsed Flow-Through Optical Absorption Detectors," Talanta, 40(1):53-74 (1993).

* cited by examiner

METHODS AND APPARATUS FOR MEASURING THE LIGHT ABSORBANCE OF A SUBSTANCE IN A SOLUTION

This application is a filing under 35 U.S.C. 371 of international application number PCT/EP2013/061212, filed May 30, 2013, which claims priority to Great Britain application number 1209738.2 filed May 31, 2012, the entire disclosure of which is hereby incorporated by reference.

The present invention relates to methods and apparatus for measuring the absorbance of light of a substance in a solution using visible or non visible light, the substance having a capacity to absorb light at a specific wavelength or wavelengths. The methods and apparatus have particular utility in detecting the concentration of proteins and nucleic acids for example where such proteins or nucleic acids are refined during liquid chromatography.

FIELD OF THE INVENTION

The invention relates to methods and apparatus for measuring the absorbance of a substance in a solution, typically a substance exhibiting UV light absorption at a wavelength of 400 nm or less.

BACKGROUND OF THE INVENTION

Many substances absorb ultra violet or visible light due to their chemical composition. The absorption of light by substances has been used as the basis for detecting the presence of, and measuring the concentration of, such substances for many years. The concentration of the substance can be determined by use of the Beer Lambert Law:

A=Ebc

Where:
A is light absorbance;
E is the molar light absorbtivity with units of $L\ mol^{-1}\ cm^{-1}$;
b is the light path length of the sample defined in cm; and
c is the concentration of the compound in solution, expressed in $mol^{-1}$.

The Emax represents the maximum absorption of a substance at a given wavelength.

The UV region can be considered to consist of light of wavelength in the region of 1 nm to 400 nm, light of wavelength of 180 nm to 300 nm being known as 'deep UV'.

Most analytical instruments for detecting substances which absorb in the deep ultra violet (UV) region use a mercury-lamp, deuterium lamp or xenon flash lamp as a light source. One example of such an instrument is a flow cell in which a solution containing one or more UV absorbing substances is passed between a UV light source (e.g. a mercury-lamp) and a UV detector (e.g. a photomultiplier or a photodiode) and changes in the intensity of UV light reaching the detector are related to the concentration of UV absorbing substances in the solution.

The detection of proteins, nucleic acids and peptides are of great importance in many sectors, including the environmental, biological and chemical sciences. Proteins have mainly two absorption peaks in the deep UV region, one very strong absorption band with a maximum at about 190 nm, where peptide bonds absorb, and another less intense peak at about 280 nm due to light absorption by aromatic amino acids (e.g. tyrosine, tryptophan and phenylalanine)

Nucleic acids absorb UV light at around 260 nm, some of the subunits of nucleic acids (purines) having an absorbance maximum slightly below 260 nm while others (pyrimidines) have a maximum slightly above 260 nm.

Almost all proteins have a maximum absorbance at about 280 nm due to the content of the light absorbing aromatic amino acids. The light source in the detectors of analytical systems used to detect and measure protein concentrations has historically been the mercury-line lamp. Mercury produces light with a wavelength of 254 nm but not at 280 nm, so a fluorescence converter is needed to transform the 254 nm light produced by the mercury lamp to longer wavelengths and a band pass filter is used to cut out a region around 280 nm. Mercury lamps have relatively short lifetimes and can prove unstable with time; furthermore, the disposal of these lamps can lead to environmental problems. The other lamps used to generate ultra violet light, such as the deuterium and the xenon flash lamps, disadvantageously require high voltages, need complicated electronics and often prove unstable with time. All of the currently used ultra violet light sources are relatively large and are consequently unsuitable for miniaturisation of analytical instruments. Moreover, all of the lamps generate significant amounts of heat due to the high voltages required for their operation.

Recently light emitting diodes (LED) of type AlGaN/GaN with emissions in the 250 nm to 365 nm range have been developed. Sensor Electronic Technology, Inc. (Columbia, S.C., USA) have pioneered the development and use of these UV light emitting diodes, particularly for irradiating and sterilising fluids such as biologically contaminated water (e.g. US 2005/0093485). Other groups have also employed UV light emitting diodes for water purification systems (e.g. Phillips Electronics, WO2005/031881).

Light emitting diodes (LEDs), which emit in the visible region of the spectrum, have been used for indirect photometric detection (Johns C., et al. (2004) Electrophoresis, 25, 3145-3152) and fluorescence detection of substances in capillary electrophoresis (Tsai C., et al. (2003) Electrophoresis, 24, 3083-3088). King et al. (Analyst (2002) 127, 1564-1567) have also reported the use of UV light-emitting diodes which emit at 379.5 nm for indirect photometric detection of inorganic anions.

The use of deep UV light emitting diodes as light sources in detection systems for nucleic acids is disclosed in US2005/0133724. However, although detection systems employing LEDs are disclosed, there are no experimental data to indicate that the proposed systems were indeed successfully employed to measure nucleic acid levels in polymerase chain reaction assay. The system described would lack sensitivity, linearity, and dynamic range because there is no use of a band pass filter or a beam splitter and reference detector; LEDs are very sensitive to minute changes in temperature, changes of the order of one hundredth of a degree Centigrade causing a drift in the baseline. Furthermore, the system lacks a band pass filter which acts to both narrow the bandwidth and block light in the visible region of the spectrum. A narrow bandwidth compared to the natural bandwidth of the sample, preferable a ratio of 1 to 10, provides a good linearity of the response and a broad dynamic range. (Practical Absorbance Spectrometry. Ed. A Knowles and C. Burgess, Chapman and Hall, New York).

JP2002005826 discloses a system for measuring ozone concentration. However, no experimental data that show the linearity and dynamic range are provided. The system uses a solid state emitter, which is composed of a diamond semiconductor thin film, to emit ultraviolet light with an emission peak of wavelength 240 to 270 nm. The emission spectrum at half value width of the UV peak is somewhat narrower than the half value width of the peak of the absorption spectrum of ozone (emission maximum approximately 254 nm). However, while this may be sufficient to measure ozone concentrations, the lack of a band pass filter which can reduce the band width to, for example, one tenth of the half value width of the ozone absorption peak will significantly reduce the linearity and dynamic range of the detector (Practical Absorbance Spectrometry. Ed. A Knowles and C. Burgess, Chapman and Hall, New York). This system also lacks a reference photo detector, so no measurement of the intensity of the emitted light is made. This means that compensation of variations of the emitted intensity due to changes in temperature is not possible.

WO2007/062800 (incorporated herein by reference), describes the use of a UV LED as a source of light for analysis of the concentration of a substance in a liquid sample, but it has been found that a broader spectrum of light is desirable in order to subject the sample to different wavelengths and thereby define a substance more accurately or more quickly, by its absorption characteristics at different wavelengths. However, known LEDs have only a limited light wavelength output range.

The present invention addresses the aforementioned problems with the currently available light sources used in analytical systems for detecting and/or for measuring the concentration of a substance in a solution.

SUMMARY OF THE INVENTION

It will be understood that the term 'substance', as used herein, refers to any chemical entity. In particular, it includes organic compounds and inorganic compounds. Examples of organic compounds include, but are not limited to, proteins, peptides, carbohydrates, lipids, nucleic acids, protein nucleic acids, drug candidates and xenobiotics. Examples of inorganic compounds include metal salts (e.g. ferric sulphate, copper chloride, nickel nitrate).

In a first aspect of the present invention, there is provided a method for measuring the light absorbance of a substance in a solution and optionally subsequently determining the concentration of said substance with or without knowing the molar absorbtivity E of the substance, the substance exhibiting light absorption, the method comprising the steps, in any suitable order, of: i) transmitting light having a first wavelength output from a first LED light source; ii) directing the light output from the LED through the substance in solution; and iii) quantifying the intensity of the light propagating from the solution to provide an indication of the concentration of the substance in the solution; the method being characterised in that the steps i) to iii) are repeated using a second LED light source having an output of a second wavelength different from the first wavelength.

According to a second aspect of the present invention, there is provided an apparatus for measuring the light absorbance of a substance in a solution, comprising: i) a sample cell of known path length for containing said solution, said cell being at least partially transparent to light of a predefined wavelength spectrum; ii) an LED light source arrangement for emitting light, within said predefined wavelength spectrum, along a light path; and optionally iii) a band pass filter in the light path; the apparatus being characterised in that said LED light source arrangement includes plural LED's each having a different wavelength light output said arrangement being operable to provide light along the light path which has a selectably different wavelength within the predefined wavelength spectrum.

According to a third aspect, the invention consists in the method of the first aspect; or use of the apparatus according to the second aspect; for determining or measuring the concentration of a substance selected from the group consisting of protein, peptide and nucleic acid.

The invention is further defined in the claims. The invention can be put into effect in numerous ways, examples of which are described in detail below, with reference to the Figures.

DETAILED DESCRIPTION OF THE INVENTION

Figure 1:
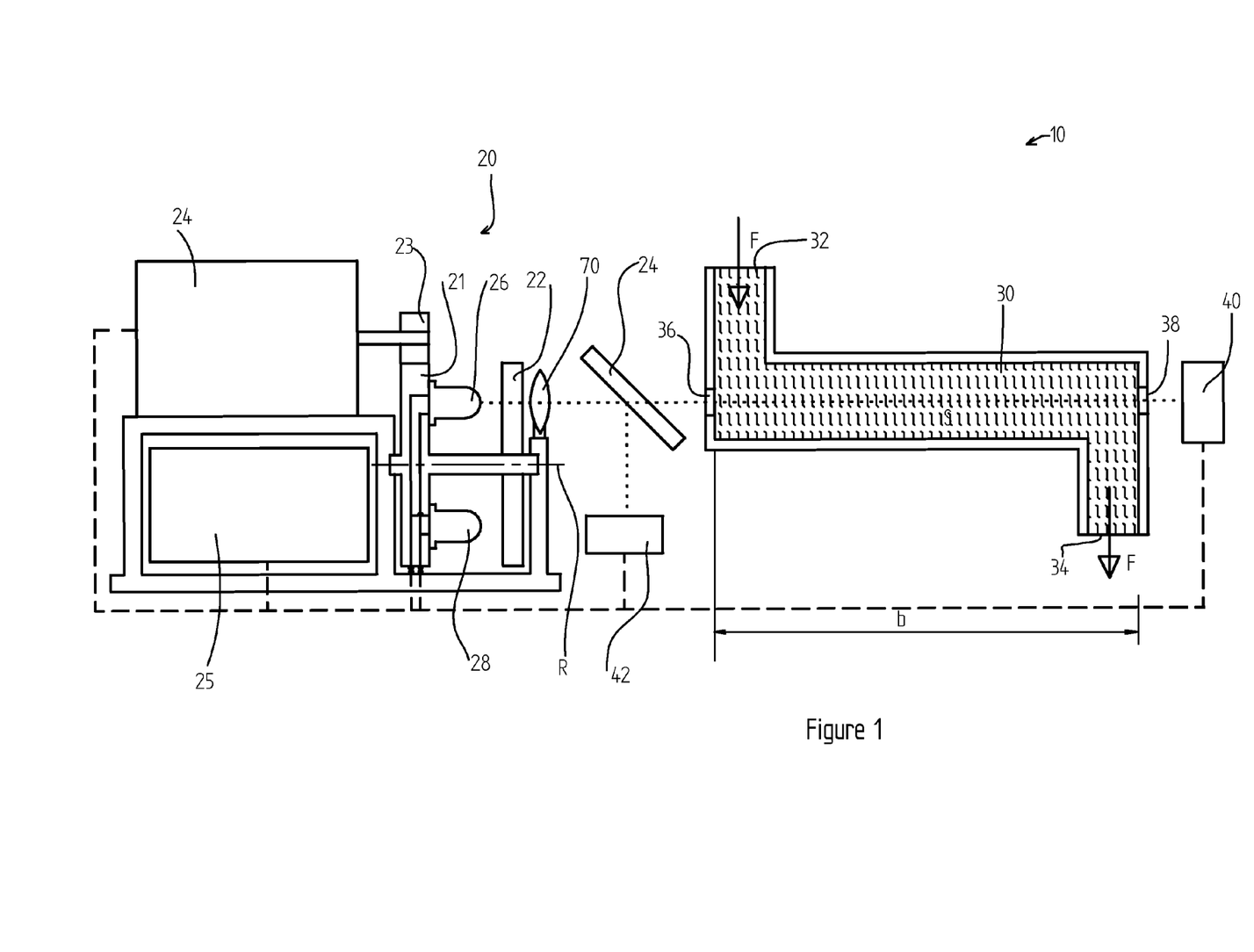
FIG. 1 is a schematic diagram showing a first embodiment of apparatus for determining the concentration of a substance in a solution.

FIG. 1 is a schematic representation of one embodiment of an apparatus according to the invention. The apparatus 10 comprises an arrangement 20 of light emitting diodes which each emit light in the ultraviolet part of the spectrum (UV LED), a flow cell 30 with an inlet 32 and an outlet 34 and photo-detectors 40,42 which can either be UV sensitive photo multipliers or UV sensitive photo diodes. The apparatus further consists of a band pass filter 22 which rejects unwanted wavelengths and admits others, while maintaining a low coefficient of absorption for the UV wavelengths of interest. The bandwidth of the filter is a full width half maximum, and is preferably less than 10 nm, to give a good linearity and large dynamic range. The apparatus further comprises a collimating lens 70 and a beam-splitter 24 which diverts a portion of the now collimated light from the LED arrangement 20 onto a reference photo detector 42 while the remainder is directed through a solution S within the flow cell 30. The beam-splitter 24 and reference photo detector 42 are used to follow any intensity changes in the UV LED arrangement 20 and thus avoid the need for complicated thermostatic control of the LED arrangement 20. However, a beam splitter and reference detector could be omitted, where a lower performance apparatus is acceptable. The flow cell 30 has windows 36 and 38 which are made from a UV transparent material such as sapphire, quartz or synthetic fused silica and is of a known path length b. Other materials, such as polymers could be used.

The solution S is passed through the flow cell 30 via the inlet 32 and the outlet 34, in the direction of arrows F, and may contain a substance with a light absorption at 300 nm or less e.g. a protein or nucleic acid. UV light from the LED arrangement 20 is used to irradiate the solution S in the flow cell 30, the light entering the flow cell 30 through the UV transparent window 36, as indicated by the chain dotted line. Light passing through the solution and exiting the window 38 is then detected by the detector photo-detector 40.

The UV LED arrangement 20 comprises a carrousel 21 rotatable about an axis R, driven by a stepper motor 24 via a spur gear pair 23. The carrousel supports plural, in this case two, UV LEDs 26 and 28. A controller 25 is used to drive the stepper motor 24 and thus to bring each LED into the correct position to irradiate the sample S in the flow cell 30. The wavelength of UV light employed to irradiate the sample can be selected by either the use of an appropriate LED which emits at a specific wavelength of UV light for example, a UVTOP® 260 nm and 280 nm LEDs. UVTOP® LEDs are available from Sensor Electronic Technology Inc., SC, USA e.g. diodes which emit in the range of 250-365 nm.

Once the absorption of the solution is measured, the concentration of the substance in the solution can then be determined by use of the Beer Lambert Law where the molar absorbtivity E of the substance is already known. This can be done manually or using a computer or the controller 25 provided. Alternatively, the concentration of the substance can be determined by use of a dose-response curve which has previously been produced for the substance of interest at a given wavelength e.g. 280 nm, or multiple response curves which are generated at different wavelengths can be used. Such determinations are made using a computer via a data link to the controller 25. In some applications, it is the change in absorbance that is of interest, for example during separation of proteins in a chromatographic column, and so there is no need to determine the concentration of the substance. In that case, the molar absorbtivity (E) need not be known. Using two frequencies of light also allows this change in absorbance to be more closely monitored when the absorbance reaches a threshold where switching to a second less absorbed light can give a better resolution of the rate of change of absorption, and consequently the approach of a maximum or minimum of concentration values.

The carrousel can be rotated to provide stepped movement of the LEDs, which dwell at the irradiating position for a predetermined time, usually about 0.25 to 3 seconds, or a continuous rotation is possible at around 1 to 20 rpm giving a period of irradiation as the LED's orbit moves through an area where such irradiation is possible.

In the embodiment described above, a carrousel 21 is shown, but it will be appreciated that non-rotary movement of the LEDs could also be used to bring the LEDs into alignment with the light path indicated by the chain dotted line in FIG. 1. For example the LEDs 26 and 28 could be mounted to a linear slideway which provides up and down motion of the LEDs to bring then into said alignment.

Figure 2:
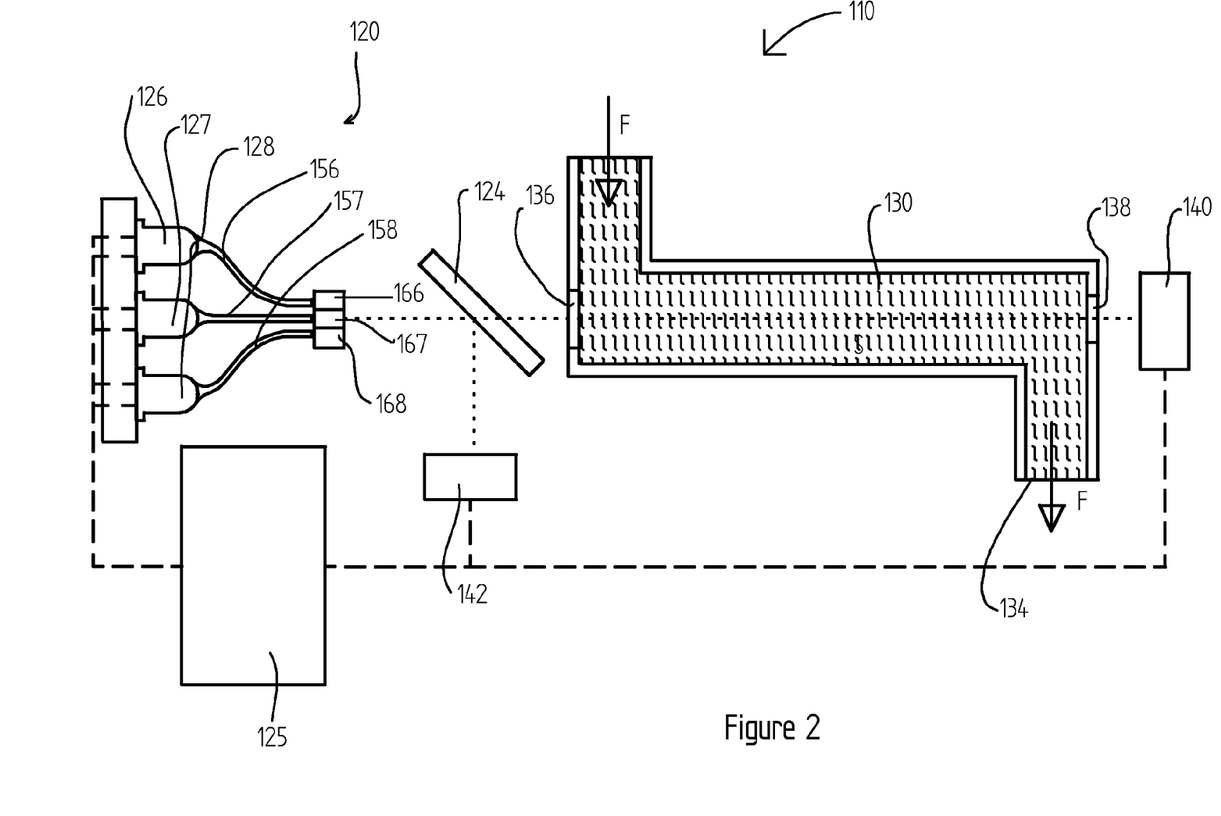
FIG. 2 is a schematic diagram showing a second embodiment of apparatus for determining the concentration of a substance in a solution.

Another embodiment of an apparatus 110 according to the invention is shown in FIG. 2. In FIG. 2, features in common with the embodiment shown in FIG. 1 have the same reference numerals, but prefixed by the numeral '1'. In the embodiment of FIG. 2, an LED arrangement 120 is shown which includes plural LEDs 126, 127, and 128, each having a respective optical coupling 156, 157 and 158, in practice an optical fibre, each terminating in close proximity, at an area suitable for irradiating the sample cell 130 via a respective band pass filter 166,167 and 168, and common beam splitter 124 operable as described above.

This embodiment functions in a similar manner to the embodiment shown in FIG. 1, except that a controller 125 provides power to each UV LED at a suitable time instead of the LEDs physically moving. This power excites a corresponding one of the LEDs 126, 127, or 128 and causes light at the desired wavelength to travel along an associated light paths, to irradiate the sample cell 130, in a manner as described above. The beam-splitter 124 and reference photo detector 142 are used to follow and compensate for any intensity changes in the LED's light output.

The ultra violet light passing through the solution S in the flow cell 130 and exiting from the window 138 is detected by the sample photo-detector 140, as described above. It will be understood by the person skilled in the art that an identical apparatus, having a flow cell 130 of unknown path length, could be used simply to detect the presence of, and changes in concentration of a substance. The determination or measurement of the concentration of the substance in solution requires knowledge of the path length cf. Beer Lambert Law.

Whilst the second embodiment requires that the UV LEDs are activated one by one, it is possible that they may be activated simultaneously. In addition, the filters 166, 167 and 168 of the second embodiment could be made to rotate such that only one filter is present at a narrow idea where the optical fibres all converge, thereby allowing only a specific waveband to pass, even if all the LEDs are illuminated.

Figure 3:
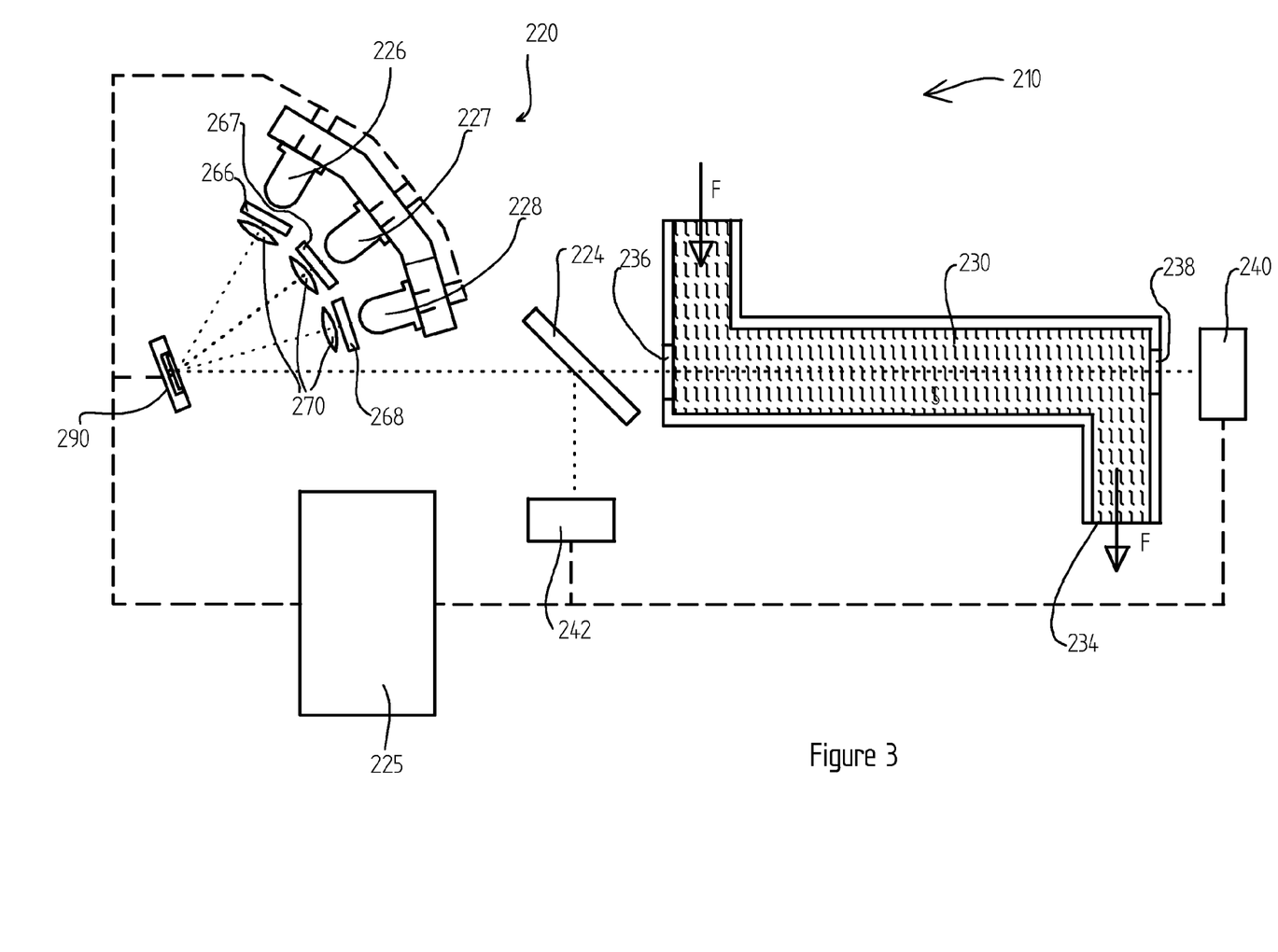
FIG. 3 is a schematic diagram showing a third embodiment of apparatus for determining the concentration of a substance in a solution.

Another embodiment of an apparatus according to the invention is shown in FIG. 3. In FIG. 3, features in common with the embodiment shown in FIG. 1 have the same reference numerals, but prefixed by the numeral '2'.

In this embodiment, apparatus 210 is shown in which UV light of different frequencies is provided by three (or more) UV LEDs 226, 227 and 228. UV light from each LED propagates through a respective band pass filter 266, 267, 268. From there, UV light can propagate to a moveable reflective surface 290. In this case the moveable reflective surface 290 is a so called micro-electro-mechanical system (MEMS) mirror, which is a mirror mounted to single chip component capable of tilting the mirror about at least one axis under the control of a controller 225, so that said light is reflected accurately toward the flow cell 230, from each LED in turn, via its respective filter and lens. MEMS mirrors are available from, for example, Mirrorcle Technologies. The apparatus otherwise functions as described above, by providing the desired wavelength of light from the desired UV LED on demand.

Figure 4:
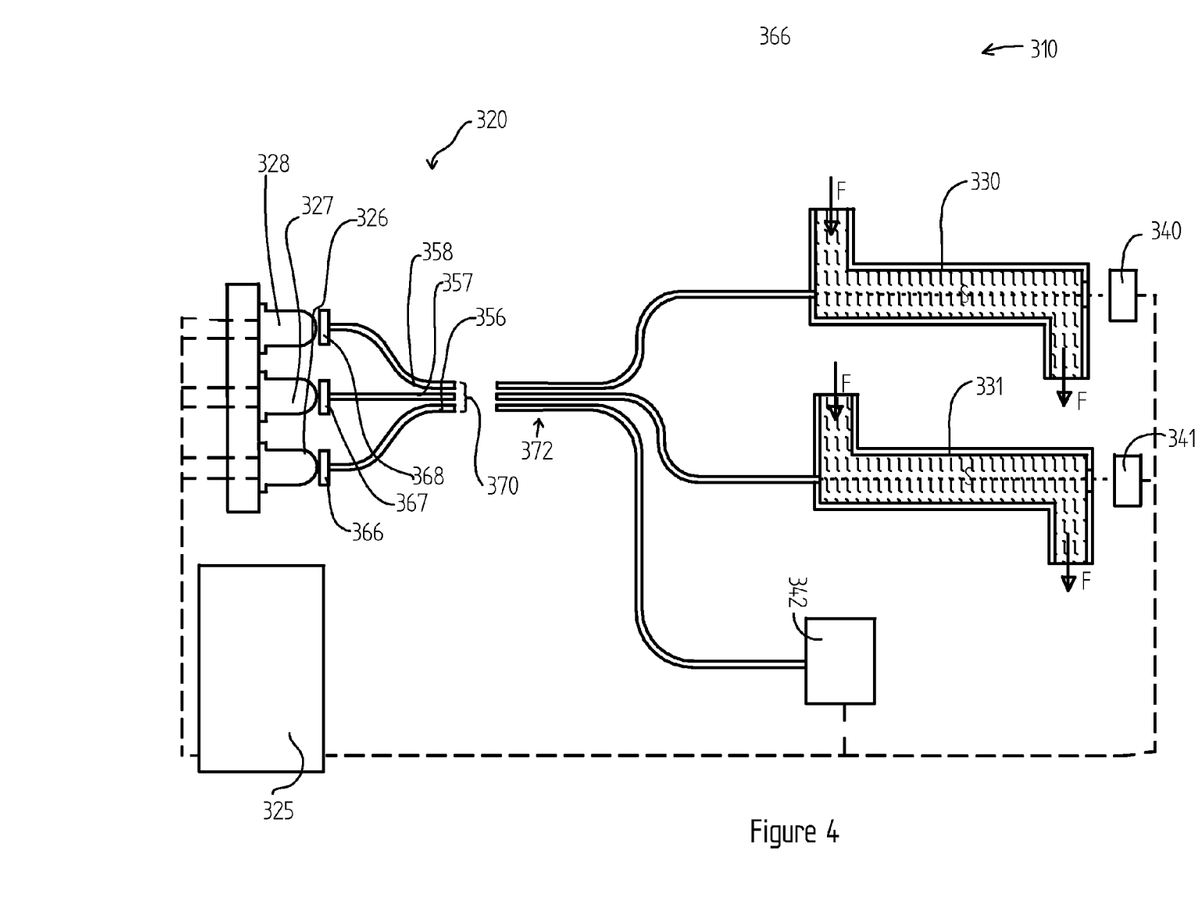
FIG. 4 is a schematic diagram showing a fourth embodiment of apparatus for determining the concentration of a substance in a solution.

FIG. 4 shows a further embodiment of an apparatus according to the invention. In FIG. 4, features in common with the embodiment shown in FIG. 1 have the same reference numerals, but prefixed by the numeral '3'.

Apparatus 310 is shown which again has plural UV light producing LEDs 326,327 and 328. Light emitted from the LEDs is separately filtered by a respective band pass filter 366, 367 and 368, and then light from each filter propagates into an optical fibre 356, 357,358. Each optical fibre is brought together to form a bundle 370. The terminal end of the bundle 370 launches light in a slightly diffuse manner from one or more of the LEDs toward a receiving optical fibre bundle 372 spaced from the bundle 370, such that light is spread out substantially evenly across the fibres of the receiving bundle 372. Whilst three optical fibres have been shown in the bundles 370 and 372, it will be apparent that this technique allows different numbers of optical fibres in each bundle. Also the drawings show the fibre spaced apart of clarity, although in practise they will be held together tightly. At the bundle 372, light is split to travel to, in this case, two flow cells 330, and 331, and also to a reference detector 342.

In this embodiment, the flow F through the flow cells 330 and 331 can be in parallel or in series, but in either case the flow can be sequentially or synchronously monitored using different UV frequencies to provide a greater range of absorbance values as the concentration of the substance in solution changes. In a modification the two flow cells may have different light path dimensions, thereby further enhancing the range of the apparatus. For example where a substance has a low absorbance at a first frequency, then a long light path can be used, and where the same substance has a high absorbance at a second frequency, then a short path length can be used.

In operation, each the embodiments rely on a controller 25,125,225,325 to control the moment when the sample is irradiated. Since it is a straight forward task to alter the point in time at which the respective UV LED provides light to the sample cell, and the apparatus employed is rugged and low cost, then the embodiments shown provide an adaptable, reliable and low cost liquid device for determining the concentration of a substance in a liquid by measuring its absorbance. It is preferred that UV LEDs emitting light up to 400 nm are used for the measurement of concentrations in solution of proteins, peptides, nucleic acids, cell extracts, cell lysates, cell cultures or combinations thereof, but the invention has application to other light wavelengths, particularly wavelengths up to 700 nm. Two or three LEDs have been shown, but more than three may be employed, for example four, or five or six or more LEDs could be used, and additional LED's could emit visible light. In the embodiments, the band pass filters have been shown to be located between the sample cells 30,130,230,330,331 and their respective LED light sources, however, the apparatus shown will function with equal effectiveness if the filters are placed after the sample cells, but before the detectors 40,140,240,340,341. In that case, the filters will need to be changed so that the correct filter is used with the correct LED. The reference detectors 42,142,242, 342 will still function to detect changes the LED output intensity even if the light falling on them is unfiltered.

The LEDs shown are schematically represented, and their form could be different to that shown. For example surface mounted LEDs could be used which are generally flatter than those shown, and have a flat collimating lens attached. So called multiple light source LEDs, which generate different frequencies of light from adjacent semiconductor areas could be employed, in which case the scale of the devices shown would be smaller, but there operating principles would be the same.

The usual mode of operation for all embodiments will be to cyclically change between wavelengths to optimise performance, however for some substances it will be possible to search for low concentrations of that substance at a first wavelength which substance even at low concentrations absorbs that light at the first frequency readily, and then, as concentrations increase, to switch to a second wavelength which is not so readily absorbed, thereby providing a greater range of operation and sensitivity.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims. For determining the scope of this disclosure, it is intended that any feature of one embodiment could be combined with a further feature or features of one or more other embodiments.

What is claimed is:

1. A method for measuring the absorbance of a substance, the method comprising:
    directing a first light beam outputted from a first light-emitting diode (LED) on the substance, the first light beam having a first wavelength;
    quantifying the intensity of the first light beam as it exits the substance;
    determining, from the quantified intensity of the first light beam, a first absorbance value of the substance;
    determining when a change in the first absorbance value reaches a threshold;
    directing, in response to the change reaching the threshold, a second light beam outputted from a second LED on the substance, the second light beam having a second wavelength different than the first wavelength;
    quantifying the intensity of the second light beam as it exits the substance; and
    determining, from the quantified intensity of the second light beam, a second absorbance value of the substance.

2. The method of claim 1, wherein the first light beam is directed through a first band pass filter corresponding to the first wavelength and wherein the second light beam is directed through a second band pass filter corresponding to the second wavelength.

3. The method of claim 1, wherein determining the first absorbance value includes (i) directing a first portion of the first light beam to a reference detector, yielding a reference value and (ii) directing a second portion of the first light beam on the substance, yielding a measured value, and (iii) computing the first absorbance based on the measured value and the reference value.

4. The method of claim 1 wherein the first and/or second LEDs are UV LEDs.

5. The method of claim 1, wherein the substance is in a solution, and the solution is selected from the group consisting of cell extract, cell lysate, cell culture, and mixtures thereof.

6. The method of claim 1, wherein the substance is selected from the group consisting of a protein, a peptide, and a nucleic acid.

7. An apparatus for measuring the absorbance of a substance, the apparatus comprising:
    a first light emitting diode (LED) configured to emit a first light beam having a first wavelength;
    a second LED configured to emit a second light beam having a second wavelength;
    a sample holder configured to hold the substance; and
    a controller programmed to:
        (i) direct the first light beam on the substance;
        (ii) quantify the intensity of the first light beam as it exits the substance;
        (iii) determine, from the quantified intensity of the first light beam, a first absorbance value of the substance;
        (iv) determine when a change in the first absorbance value reaches a threshold;
        (v) direct, in response to the change reaching the threshold, a second light beam outputted from a second LED on the substance, the second light beam having a second wavelength different than the first wavelength;
        (vi) quantify the intensity of the second light beam as it exits the substance; and
        (vii) determine, from the quantified intensity of the second light beam, a second absorbance value of the substance.

8. The apparatus of claim 7, wherein the apparatus further includes a beam splitter, a reference detector, and a sample detector.

9. The apparatus of claim 7, wherein one of the first LED and the second LED is a UV LED.

10. The apparatus of claim 7, further including a moveable support supporting the first LED and the second LED.

11. The apparatus of claim 10, wherein the support comprises a rotatable carousel supporting each of the first LED and the second LED.

12. The apparatus of claim 10, wherein the support is configured to move linearly.

13. The apparatus of claim 7, further comprising a moveable reflective surface.

14. The apparatus of claim 7, further comprising an optical fiber associated with the first LED and an optical fiber associated with the second LED.

15. The apparatus of claim 7, further comprising a first filter and a second filter associated with the first LED and the second LED, respectively.

\* \* \* \* \*